US00PP16448P2

(12) United States Plant Patent
Gitzels

(10) Patent No.: US PP16,448 P2
(45) Date of Patent: Apr. 18, 2006

(54) ***DAHLIA* PLANT NAMED 'BALDELEMZ'**

(50) Latin Name: *Dahlia variabilis*
Varietal Denomination: Baldelemz

(75) Inventor: Jeroen Gitzels, Zwaag (NL)

(73) Assignee: Ball Horticultural Company, West Chicago, IL (US)

( * ) Notice: Subject to any disclaimer, the term of this patent is extended or adjusted under 35 U.S.C. 154(b) by 163 days.

(21) Appl. No.: 11/016,489

(22) Filed: Dec. 17, 2004

(51) Int. Cl.
*A01H 5/00* (2006.01)

(52) U.S. Cl. ..... Plt./321
(58) Field of Classification Search ..... Plt./321
See application file for complete search history.

*Primary Examiner*—Kent Bell
(74) *Attorney, Agent, or Firm*—Wood, Phillips, Katz, Clark & Mortimer

(57) ABSTRACT

A new and distinct *Dahlia* named 'Baldelemz', characterized by its double deep yellow-colored ray florets, yellow-colored disc florets, and vigorous, upright, and mounded growth habit.

1 Drawing Sheet

Latin name of genus and species of plant claimed: *Dahlia variabilis*.
Variety denomination: 'Baldelemz'.

BACKGROUND OF THE INVENTION

The present invention relates to a new and distinct *Dahlia* plant botanically known as *Dahlia variabilis* and hereinafter referred to by the cultivar name 'Baldelemz'.

The new cultivar originated in a controlled breeding program in Enkhuizen, The Netherlands during July 1999. The objective of the breeding program was the development of freely flowering *Dahlia* cultivars with large inflorescences and a vigorous, upright growth habit.

The new cultivar was the result of the open-pollination of the proprietary breeding selection designated '3385', not patented, characterized by its yellow-colored inflorescences. Seed from the above stated open-pollination was germinated and grown to maturity. One plant within the progeny was discovered and selected by the inventor during May 2000 at Enkhuizen, The Netherlands.

Asexual reproduction of the new cultivar by terminal stem cuttings taken since May 2000 at Enkhuizen, The Netherlands and West Chicago, Ill. has demonstrated that the new cultivar reproduces true to type, with all characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment such as temperature, light intensity, and day length without, however, any variance in genotype.

The following characteristics of the new cultivar have been repeatedly observed and can be used to distinguish 'Baldelemz' as a new and distinct cultivar of *Dahlia* plant:

1. Double inflorescence form.
2. Deep yellow-colored ray florets and yellow-colored disc florets.
3. Vigorous, upright, and mounded growth habit.

Plants of the new cultivar differ from plants of the female parent primarily in inflorescence color and floriferousness.

Of the many *Dahlia* cultivars known to the inventor, the most similar to the new cultivar is the cultivar 'Margaret Improved', U.S. Plant Pat. No. 14,202. However, in side by side comparisons, plants of the new cultivar differ from plants of 'Margaret Improved' in the following characteristics:

1. Plants of the new cultivar exhibit lighter foliage color than do plants of 'Margaret Improved'.
2. Plants of the new cultivar exhibit smaller inflorescences than do plants of 'Margaret Improved'.

BRIEF DESCRIPTION OF THE PHOTOGRAPHS

The accompanying photographs show, as nearly true as it is reasonably possible to make the same in color illustrations of this type, typical inflorescence and foliage charateristics of the new cultivar. Colors in the photographs differ slightly from the color values cited in the detailed description, which accurately describes the colors of the new cultivar. The plants were grown for 11 weeks in a greenhouse at West Chicago, Ill.

DETAILED BOTANICAL DESCRIPTION

Figure 1:
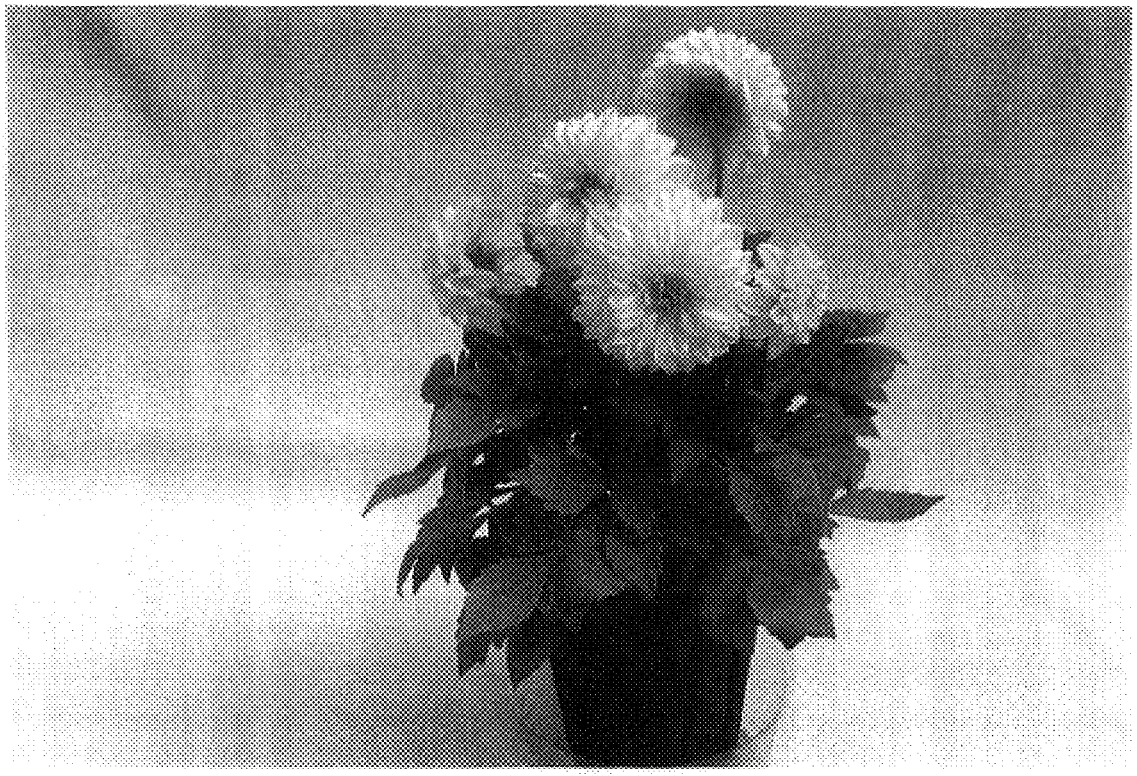
FIG. 1 illustrates a side view of the overall growth and flowering habit of 'Beldelemz'.
Figure 2:
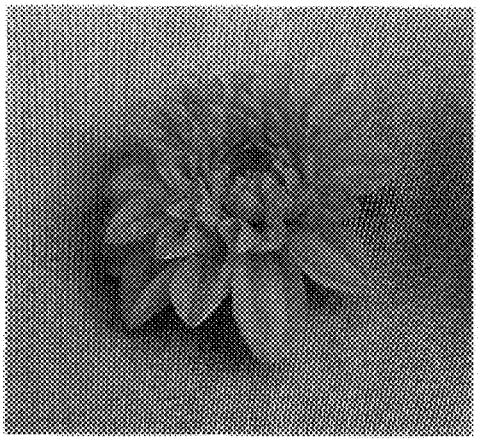
FIG. 2 illustrates a close-up view of a single inflorescence of 'Beldelemz' just opening.
Figure 3:
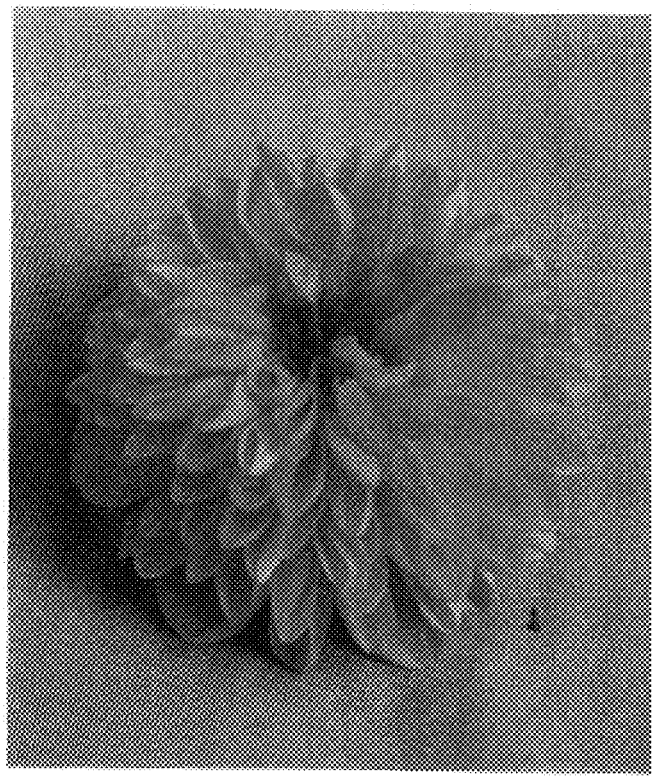
FIG. 3 illustrates a single fully open inflorescence of 'Beldelemz'.

The chart used in the identification of colors described herein is The R.H.S Colour Chart of The Royal Horticultural Society, London, England, 2001 edition, except where general color terms of ordinary significance are used. The color values were determined on Oct. 15, 2004 between 10:00 and 11:45 a.m. under natural light conditions in West Chicago, Ill.

The following descriptions and measurements describe plants produced from cuttings taken from stock plants and grown in a double polycarbonate-covered greenhouse in West Chicago, Ill. under conditions comparable to those used in commercial practice. The plants were grown in 10 cm pots for 11 weeks while utilizing a soil-less growth medium. Greenhouse temperatures were maintained at approximately 65°–75° F. (18°–24° C.) during the day and approximately 60°–65° F. (15°–18° C.) during the night. Greenhouse light levels were maintained at approximately 4,000–6,000 footcandles during the day. Plants were pinched three weeks after planting of rooted cuttings.

Botanical classification: *Dahlia variabilis* cultivar Baldelemz.

Parentage: Open-pollination of the proprietary *Dahlia* breeding selection designated '3385', not patented.

Propagation:

*Type cutting.*—Terminal tip.

*Time to initiate roots.*—Approximately 7 to 10 days.

*Time to produce a rooted cutting.*—Approximately 21 to 28 days.

*Rooting habit.*—Freely branching.

*Root description.*—Fine, fibrous.

*Tubers.*—Will form under short day conditions of at least 13 to 14 hours of darkness.

Plant description:

*Crop time.*—Approximately 8–10 weeks.

*Growth habit.*—Basal branching, pinching enhances branching.

*General appearance and form.*—Upright, mounded and vigorous.

*Size.*—Height from top of soil to top of plant plane: Approximately 21.6 cm. Width/area of spread: Approximately 28.5 cm.

*Branch description.*—Quantity per plant: Approximately 4. Strength: Strong. Length: Approximately 9.7 cm. Diameter: Approximately 7.4 mm. Length of center internode: Approximately 1.9 cm. Texture: Glabrous. Color: 145A.

*Foliage.*—Quantity of leaves per lateral branch: Approximately 16. Type: Simple and compound. Quantity of leaflets per compound leaf: 3. Fragrance: None. Arrangement: Opposite. Aspect: At acute angle to stem. Leaf/leaflet: Shape: Ovate. Apex: Acute. Base: Attenuate. Margin: Dentate. Venation pattern: Pinnate. Color of upper surface of all leaves/leaflets: Closest to 137B with venation of 137C. Color of lower surface of all leaves/leaflets: Closest to but lighter than 147B with venation of 137C. Texture of upper surface of all leaves/leaflets: Glabrous with some pubescence along margin. Texture of lower surface of all leaves/leaflets: Sparse pubescence along veins. Length of simple leaf: Approximately 4.5 cm. Width of simple leaf: Approximately 2.1 cm. Length of petiole of simple leaf: Approximately 1.5 cm. Diameter of petiole of simple leaf: Approximately 2 mm. Texture of petiole of simple leaf: Sparsely pubescent. Color of petiole of simple leaf: 145A. Length of mature trifoliate leaf: Approximately 8.1 cm. Width of mature trifoliate leaf: Approximately 6.1 cm. Length of petiole of mature trifoliate leaf: Approximately 4 cm. Diameter of petiole of mature trifoliate leaf: Approximately 2 mm. Texture of petiole of mature trifoliate leaf: Sparsely pubescent. Color of petiole of mature trifoliate leaf: 145A. Length of terminal leaflet: Approximately 6 cm. Width of terminal leaflet: Approximately 2.5 cm. Length of petiole of terminal leaflet: Approximately 1.5 cm. Diameter of petiole of terminal leaflet: Approximately 2.5 mm. Length of lateral leaflet: Approximately 5.1 cm. Width of lateral leaflet: Approximately 2.1 cm. Petiole of lateral leaflet: Absent.

Flowering description:

*Outdoor flowering habit.*—'Baldelemz' is freely flowering under outdoor growing conditions with substantially continuous blooming from spring through autumn and year round in greenhouse environment.

*Time to first flower.*—Approximately 8 weeks.

Inflorescence description:

*Appearance.*—Type: Composite. Form: Fully double, arising from leaf axils on strong peduncles, positioned just over the foliage. Disc and ray florets arranged acropetally on a capitulum. Persistent.

*Quantity per plant.*—Approximately 2 fully open at any one time.

*Lastingness of bloom.*—Approximately 4 weeks from first open ray floret to senescence.

*Shape/size.*—Hemispherical. Diameter: Approximately 5.6 cm. Depth: Approximately 2 cm. Disc diameter: Approximately 1 cm. Receptacle diameter: Approximately 9 mm. Receptacle height/depth: Approximately 4 mm. Receptacle color: 144C.

*Flower bud.*—Quantity showing color per plant: Approximately 2. Rate of opening: Generally takes approximately 2 weeks for buds to progress from first color to fully open inflorescence. Quantity per plant: Approximately 2 showing color at any one time. Shape: Oblate. Length at first color: Approximately 1 cm. Width at first color: Approximately 1.2 cm. Texture: Glabrous. Color: 3A.

*Fragrance.*—None.

*Ray florets.*—Quantity: Approximately 45 per inflorescence. Shape: Obovate, cupped. Apex: Emarginate. Base: Attenuate, fused to form tube. Margin: Entire. Length: Approximately 2.5 cm. Width: Approximately 1.4 cm. Texture: Glabrous. Color: Fully opened, upper surface: 2A. Fully opened, lower surface: 2A.

*Disc florets.*—Quantity: Approximately 32. Shape: Elongated, cylindrical. Apex: 5 acute tips. Length: Approximately 5 mm. Diameter at apex: Approximately 3 mm. Diameter at base: Approximately 1 mm. Texture: Glabrous. Color: Transparent, closest to 9A at apex, 150D at base.

*Peduncle.*—Strength: Strong. Aspect: Erect. Length: Approximately 5.1 cm. Diameter: Approximately 2.4 mm. Texture: Glabrous. Color: 145A.

*Phyllaries.*—Quantity: One per ray floret. Shape: Lanceolate. Apex: Emarginate with three tips. Base: Truncate. Margin: Entire. Length: Approximately 1 cm. Width: Approximately 5 mm. Texture: Glabrous, papery. Color of upper and lower surfaces: 154C, transparent.

*Secondary phyllaries.*—Quantity: Approximately 5. Shape: Lanceolate. Apex: Acute. Base: Attenuate. Margin: Entire. Length: Approximately 8 mm. Width: Approximately 3.5 mm. Texture: Glabrous. Color of upper and lower surfaces: Closest to 138A.

*Reproductive organs.*—Androecium — On disc florets. Stamen number: 5. Anther shape: Linear. Anther length: Approximately 4 mm. Anther color: 165B. Pollen amount: Abundant. Pollen color: 17B. Gynoecium — On disc and ray florets. Pistil length: Approximately 1.4 cm. Stigma length: 3 mm. Stigma color: 16A. Style length: 9 mm. Style color: 2B. Ovary length: 2 mm. Ovary color: 154C.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Baldelemz', substantially as herein shown and described.

* * * * *